United States Patent [19]
Gewald et al.

[11] Patent Number: 5,869,713
[45] Date of Patent: Feb. 9, 1999

[54] (+)- OR (−) -8-HALOGEN-6-HYDROXY-OCTANOIC ACID, ITS SALTS AND ESTERS, AND PROCESS FOR MAKING

[75] Inventors: Rainer Gewald, Dresden; Gunter Laban, Langebrück; Thomas Beisswenger, Radebeul, all of Germany

[73] Assignee: Arzneimittelwerk Dresden GmbH, Germany

[21] Appl. No.: 705,591

[22] Filed: Aug. 29, 1996

[30] Foreign Application Priority Data

Sep. 13, 1995 [DE] Germany .................. 195 33 882.0

[51] Int. Cl.⁶ .................................................. C07C 59/115
[52] U.S. Cl. ............................................ 554/108; 554/213
[58] Field of Search ...................... 554/213, 108

[56] References Cited

PUBLICATIONS

Woster, et al., J. Med. Chem., 32(6), 1300–07, 1989.
Acker, et al., J. Am. Chem. Soc., 79(24), 6483–87, Dec. 1957.
Takagi, et al., J. Chromatogr. Sci., 27(10), 574–7 *Abstract*, 1989.

*Primary Examiner*—Robert Gerstl
*Attorney, Agent, or Firm*—Schweitzer Cornman Gross & Bondell LLP

[57] ABSTRACT

The invention relates to (+) and (−)-8-halogen-6-hydroxy-octanoic acid enantiomers wherein the halogen is Cl, Br, or I, and their respective preparatory processes.

3 Claims, No Drawings

(+)- OR (−)-8-HALOGEN-6-HYDROXY-OCTANOIC ACID, ITS SALTS AND ESTERS, AND PROCESS FOR MAKING

FIELD OF THE INVENTION

The invention relates to new (+)- and (−)-8-halogen-6-hydroxy-octanoic acid enantiomers, of formula (I), wherein halogen is chlorine, bromine or iodine, their alkyl esters of formula (II) and their salts with optically active α-methylbenzylamine of formula (III) as intermediates for the synthesis of enantiomerically pure α-liponic acids of formula (IV) as well as of enantiomerically pure dihydroliponic acids of formula (V). α-Liponic acid is 1,2-dithiolan-3-pentanoic of formula thioctic acid).

BACKGROUND

The R enantiomer of α-liponic acid is a natural product, which occurs in small concentrations in practically all animal and plant cells. α-Liponic acid is of vital importance as a coenzyme of the oxidative decarboxylation of α-ketocarboxylic acids, such as pyroracemic acid. The racemate of α-liponic acid is pharmacologically active and has antiphlogistic and antinociceptive (analgesic) as well as cyto-protective properties. An important medicinal indication is the treatment of diabetic polyneuropathy. According to more recent results, as published, for example in CA 116: 207360, α-liponic acid can be of importance as a remedy for diseases caused by HIV-1 and HTLV IIIB viruses.

In the case of the pure optical isomers of α-liponic acid, the R and S forms, that is, R-α-liponic acid and S-α-liponic acid, the R enantiomer, contrary to the racemate, predominantly has antiphlogistic activity and the S enantiomer predominantly has antinociceptive activity as detailed in European patent No. 427,2447, of Nov. 8, 1990. For this reason, the synthesis of the pure enantiomers is of great importance.

Known methods for synthesizing enantiomerically pure α-liponic acid comprise splitting the racemate of α-liponic acid or its intermediates, asymmetric syntheses using chiral auxiliaries, so called "chiral pool" syntheses involving the use of naturally occurring, optically active starting compounds, as well as microbial syntheses, as referred to in survey articles of J. S. Yadav et al., J. Sci. Ind. Res. 1990, 49, 400; E. Walton et al., J. Am. Chem. Soc. 1955, 77, 5144; D. S. Acker and W. J. Wayne, J. Am. Chem. Soc. 1957, 79 6483; L. G. Chebotareva and A. M. Yurkevich, Khim.-Farm. Zh. 1980, 14, 92, A. G.; Tolstikov et al., Bioorg. Khim. 1990, 16, 1670; L. Dasaradhi et al., J. Chem. Soc., Chem. Commun. 1990, 729; A. S. Gopalan et al., J. Chem. Perkin Trans. 1 1990, 1897; A. S Gopalan et al., Tetrahedron Letters 1989, 5705; and in European patent No. 487,986 A2, 14, of Nov. 14, 1991).

Racemate splitting by forming diastereoisomeric salts of α-liponic acid with optically active α-methylbenzylamine, as described in German published patent application No. 44137773.7, of Nov, 16, 1991, represents the most economic variation so far. However, the disadvantage of this method is that the separation of the racemate takes place only in the last step of the synthesis sequence and that the undesirable enantiomers of a-liponic acid can neither be racemized nor inverted. In other known methods of splitting the racemic intermediate of α-liponic acid, in each case only one enantiomer can be converted into the desired optical isomer of α-liponic acid. Accordingly, only a theoretical yield of 50% can be attained as described by E. Walton et al., J. Am. Chem. Soc. 1955, 77; 5144, D. S. Acker and W. J. Wayne, J. Am. Chem. Soc. 1957, 79, 6483; and L. G. Chebotareva and A. M. Yurkevich, Khim.-Farm. Zh. 1980, 14, 92).

SUMMARY OF THE INVENTION

It is an object of the invention to provide intermediates for the synthesis of enantiomerically pure α-liponic acids and dihydroliponic acids, with the help of which an enantiomer of α-liponic acid or dihydroliponic acid can be synthesized with a theoretical yield of 100%.

The starting materials for the synthesis of the intermediates, the racemic 8-chloro-6-hydroxy-octanoic acid and the racemic 8-bromo-6-hydroxy-octanoic acid of formula (I), wherein X is Cl, Br, or I, are obtained by known methods by the hydrolysis of their racemic alkyl esters of formula (II), wherein X is Cl, Br, or I, and R is $C_{2-6}$ alkyl, as described by Y. Deguchi and K Nakanishi, Yakugaku Zasshi 1963, 83, 701. The racemic 8-iodo-6-hydroxy-octanoic acid of formula (I), wherein X is I is synthesized in high yield by the reaction of racemic 8-chloro-6-hydroxy-octanoic acid of formula (I) wherein X is Cl, with sodium iodide in acetone.

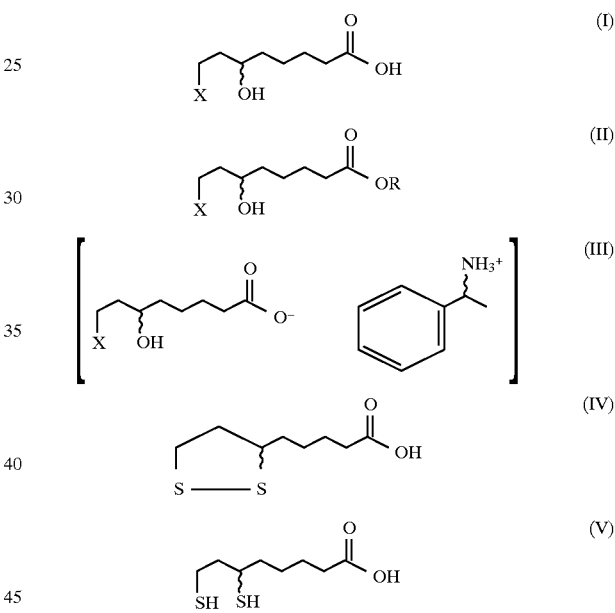

The synthesis of salts of formula (III), wherein X is Cl, Br, or I, of the pure optical isomers of 8-halogen-6-hydroxy-octanoic acids with the pure, optical isomers of α-methylbenzylamine is carried out by dissolving the isomers in a suitable solvent at an elevated temperature, such as from about 30° C. to about 100° C. and suitably from about 40° C. to about 60° C. and isolating the pure diastereoisomeric salts by crystallization at from about 10° C. to about 30° C. most suitably at about 20° C. In addition, water, $C_{3-10}$ aliphatic hydrocarbons, aromatic hydrocarbons which are liquids, $C_{2-6}$ esters of aliphatic or cycloaliphatic carboxylic acids, and $C_{2-6}$ or cycloaliphatic alcohols, $C_{1-6}$ aliphatic or cycloaliphatic alcohols ethers, and glycol ethers or homogeneous mixtures of the aforementioned solvents, are suitable as solvents. Ethyl acetate, cyclohexane, toluene, ethanol and their homogeneous mixtures are particularly suitable as solvents.

Surprisingly, there are considerable solubility differences between the diastereoisomeric salts so that a diastereoisomeric salt of formula (III) is isolated selectively and preferentially, from the reaction of the racemate of 8-halogen-6-hydroxy-octanoic acid of formula (I) with an optically pure isomer of α-methylbenzylamine. It is particularly advantageous to add only from about 0.3 to about 0.8 and suitably only from about 0.5 to about 0.6 molar equivalents of a pure enantiomer of the α-methylbenzylamine to solutions of racemic 8-halogen-6-hydroxy-octanoic acid. In so doing, a diastereoisomeric salt can be selectively isolated. The concentration of the enantiomer of the corresponding 8-halogen-6-hydroxy-octanoic acid, now present in excess in the mother liquor, can be increased especially by the addition of the other enantiomer of the α-methylbenzylamine. This procedure is suitable for a continuous method for synthesizing (+)-8-halogen-6-hydroxy-octanoic acids as well as (−)-8-halogen-6-hydroxy-octanoic acids, the two pure enantiomers being obtained largely without any loss. These diastereoisomeric salts can be purified by recrystallization from the pure, already mentioned solvents or their homogeneous mixtures, so that the salts finally are present in pure form.

The pure salts of formula (III) of (+)-8-halogen-6-hydroxy-octanoic acid and R-(+)-α-methylbenzylamine, or (−)-8-halogen-6-hydroxy-octanoic acid, and S-(−)-α-methylbenzylamine, obtained by the separation steps identified above, can be split by the addition of acids, such as mineral acids, or bases, such as alkali hydroxides and the pure (+)-8-halogen-6-hydroxy-octanoic acids or the pure (−)-8-halogen-6-hydroxy-octanoic acids can be isolated by extraction.

Pursuant to the invention, the enantiomers of 8-halogen-6-hydroxy-octanoic acids of formula (I) can be stereospecifically converted with retention of the configuration in the presence of catalytic amounts of HCl into the alkyl esters of formula (II), suitably their methyl esters. The reaction is suitably carried out at from about 50° to about 100° C. and most suitably at about 60° C. in the appropriate alcohol as solvent.

The purity of the optical isomers and of the diastereoisomeric salts was determined by means of the specific optical rotation. Furthermore, the relative contents of the optical isomers of the 8-halogen-6-hydroxy-octanoic acid of formula (I) and of the α-liponic acid of formula (IV) was determined by HPLC on optically active columns with a limit of detection of 0.5%. In addition, the optical purity of the esters of the 8-halogen-6-hydroxy-octanoic acids of formula (II), which were formed by the reaction with (S)-(+)-O-acetyl mandelic acid, was determined by $^1$H-NMR analysis.

The present invention enables the production of and (+)- and (−)-8-halogen-6-hydroxy-octanoic acid enantiomers of formula (I), wherein, halogen is chlorine, bromine, or iodine, their alkyl esters of formula (II) and their salts with optically active α-methylbenzylamine of formula (III) as intermediates for the synthesis of enantiomerically pure α-liponic acids of formula (IV) as well as of the enantiomerically pure dihydroliponic acids of formula (V) in a simple and economic manner in high chemical and optical yields.

The reaction scheme of the synthesis of R(+)-α-liponic acid is shown below as an example of the synthesis of enantiomerically pure α-liponic acid or dihydroliponic acid from the intermediates of the present invention. The individual reactions can be carried out by means of methods known for the respective racemate.

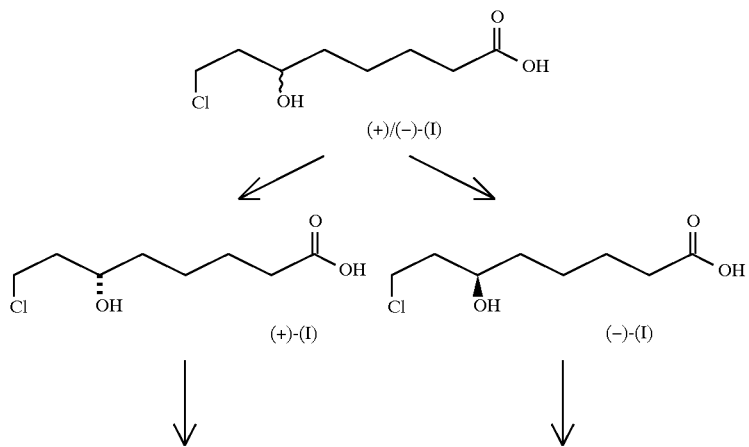

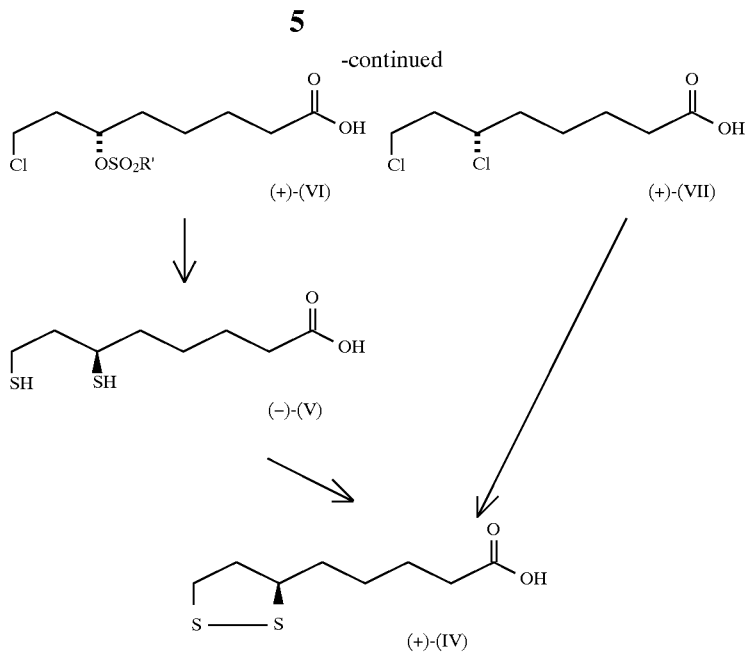

The S(−)-liponic acid is accessible in an analogous manner by using (−)8-chloro-6-hydroxy-octanoic acid for the reactions on the left side of the reaction scheme illustration, while (+)-8-chloro-6-hydroxy-octanoic acid is used for the reactions on the right side. The enantiomerically pure dihydroliponic acids can be prepared by the reduction of the corresponding enantiomerically pure a-liponic acids by methods known per se.

The invention is further illustrated in greater detail by the following examples.

EXAMPLE 1

(+)-8-Chloro-6-hydroxy-octanoic acid of formula (+)-(I), wherein X is Cl, (1.94 g, 10 mmoles) was dissolved at 60° C. in 30 ml of a 1:1 mixture of ethyl acetate and cyclohexane. Over a period of 5 minutes, 1.21 g (10 mmoles) of R-(+)-α-methylbenzylamine were added. The reaction mixture was cooled to 20° C. over a period of 1 hour. The precipitate was filtered off and washed twice with 3 ml of a 1:1 mixture of ethyl acetate and cyclohexane. The salt was dried under vacuum at 40° C.

The R-(+)-α-methylbenzylamine salt of (+)-8-chloro-6-hydroxy-octanoic acid of formula (+)/(+)-(III), wherein X is Cl, was obtained in a yield of 3.12 g (99% of the theoretical yield); $[\alpha]_D^{20}=+22.7°$ (c=1; ethanol), enantiometric excess (e.e.)>99% (HPLC), solubility in a 1:1 mixture of ethyl acetate and cyclohexane: 0.09% (20° C.), solubility in a 3:1 mixture of ethyl acetate and cyclohexane: 0.16% (20° C.), melting point: 122°–124° C.

EXAMPLE 2

(−)-8-Chloro-6-hydroxy-octanoic acid of formula (−)-(I), wherein X is Cl, (1.94 g, 10 mmoles) was dissolved at 60° C. in 30 ml of a 1:1 mixture of ethyl acetate and cyclohexane. Over a period of 5 minutes, 1.21 g (10 mmoles) of R-(+)-α-methylbenzylamine were added. The reaction mixture was cooled to 20° C. over a period of 1 hour. The precipitate was filtered off and washed twice with 3 ml of a 1:1 mixture of ethyl acetate and cyclohexane. The salt was dried under vacuum at 40° C.

The R-(+)-α-methylbenzylamine salt of (−)-8-chloro-6-hydroxy-octanoic acid of formula (−)/(+)-(III), wherein X is Cl, was obtained in a yield of 3.05 g (97% of the theoretical yield); $[\alpha]_D^{20}=+10.3°$ (c=1; ethanol), enantiomeric excess: >99% (HPLC), solubility in a 1:1 mixture of ethyl acetate and cyclohexane: 0.30% (20° C.), solubility in a 3:1 mixture of ethyl acetate and cyclohexane: 0.54% (20° C.), melting point: 94° C.–95° C.

EXAMPLE 3

(−)-8-Chloro-6-hydroxy-octanoic acid of formula (−)-(I), wherein X is Cl, (1.94 g, 10 mmoles) was dissolved at 60° C. in 30 ml of a 1:1 mixture of ethyl acetate and cyclohexane. Over a period of 5 minutes, 1.21 g (10 mmoles) of S-(−)-α-methylbenzylamine were added and the reaction mixture was worked up as described in Example 1.

The S-(−)-α-methylbenzylamine salt of (−)-8-chloro-6-hydroxy-octanoic acid of formula (−)/(−)-(III), wherein X is Cl, was obtained in a yield of 3.11 g (99% of the theoretical yield); $[\alpha]_D^{20}=-22.7°$ (c=1; ethanol), e.e >99% (HPLC), solubility in a 1:1 mixture of ethyl acetate and cyclohexane: 0.09% (20° C.), solubility in a 3:1 mixture of ethyl acetate and cyclohexane: 0.16% (20° C.), melting point: 122°–124° C.

EXAMPLE 4

(+)-8-Chloro-6-hydroxy-octanoic acid of formula (+)-(I), wherein X is Cl, (1.94 g, 10 mmoles) was dissolved at 60° C. in 30 ml of a 1:1 mixture of ethyl acetate and cyclohexane. Over a period of 5 minutes, 1.21 g (10 mmoles) of S-(−)-α-methylbenzylamine were added and the reaction mixture was worked up as described in Example 1.

The S-(−)-α-methylbenzylamine salt of (+)-8-chloro-6-hydroxy-octanoic acid of formula (+)/(−)-(III), wherein X is Cl, was obtained in a yield of 3.04 g (97% of the theoretical yield); $[\alpha]_D^{20}=-10.3°$ (c=1; ethanol), e.e.>99% (HPLC), solubility in a 1:1 mixture of ethyl acetate and cyclohexane: 0.30% (20° C.), solubility in a 3:1 mixture of ethyl acetate and cyclohexane: 0.54% (20° C.), melting point: 94°–95° C.

EXAMPLE 5

Racemic 8-chloro-6-hydroxy-octanoic acid of formula (+)/(−)-(I), wherein X is Cl, (39.9 g, 204 mmoles) was dissolved at 40° C. in 155 ml of a 1:1 mixture of ethyl acetate and cyclohexane. Over a period of 10 minutes, 13.5 g (112 mmoles) of R-(+)-α-methylbenzylamine were added. Then the mixture was cooled over a period of 2 hours to 20° C. and filtered and the precipitate was washed with 20 ml of a 1:1 ethyl acetate/cyclohexane solvent mixture and then with 30 ml of cyclohexane. The salt was recrystallized twice from 400 ml of 3:1 ethyl acetate/cyclohexane and dried under vacuum at 40° C. The (+)(+)-diastereoisomeric salt was obtained in a yield of 20.5 g, $[\alpha]_D^{20}$=+22.7° (c=1; ethanol).

The salt was suspended at 20° C. in 220 ml of diethylether and cooled in ice, after which the pH was slowly adjusted to a value of 1 with 3N hydrochloric acid and stirring, with the salt going into solution. After a further 30 minutes, the phases were separated and the organic phase washed once with 20 ml of 2N HCl and twice with 20 ml of water and dried over magnesium sulfate. After removal of the solvent under vacuum, 10.8 g (54% of the theoretical yield) of (+)-8-chloro-6-hydroxy-octanoic acid of formula (+)-(I), wherein X is Cl, were obtained; $[\alpha]_D^{20}$=+24.5° (c=1; ethanol), (e.e.) >99% (HPLC), melting point: 29°–30° C.

EXAMPLE 6

Racemic 8-chloro-6-hydroxy-octanoic acid of formula (+)/(−)-(I), wherein X is Cl, (33.9 g, 173 mmoles) was dissolved at 40° C. in 130 ml of a 1:1 mixture of ethyl acetate and cyclohexane. Over a period of 10 minutes, 11.5 g (95 mmoles) of S-(−)-α-methylbenzylamine were added. Subsequently, the mixture was cooled over a period of 2 hours to 20° C. and filtered and the precipitate was washed with 17 ml of the 1:1 ethyl acetate/cyclohexane solvent mixture and then with 25 ml of cyclohexane. The salt was recrystallized twice from 340 ml of 3:1 ethyl acetate/cyclohexane and dried under vacuum at 40° C. The (−)(−)-diastereoisomeric salt was obtained in a yield of 17.2 g, $[\alpha]_D^{20}$=−22.7° (c=1; ethanol).

The salt was suspended at 20° C. in 190 ml of diethyl ether and cooled in ice, after which the pH was slowly adjusted with 3N hydrochloric acid to 1 while stirring, the salt was going into solution. After a further 30 minutes, the phases were separated and the organic phase washed once with 17 ml of 2N HCl and twice with 20 ml of water and dried over magnesium sulfate. After removal of the solvent under vacuum, 9.1 g (53% of the theoretical yield) of (−)-8-chloro-6-hydroxy-octanoic acid of formula (−)-(I), wherein X is Cl, were obtained; $[\alpha]_D^{20}$=−24.5° (c=1; ethanol), e.e. >99% (HPLC), melting point: 29°–30° C.

EXAMPLE 7

(+)-8-Chloro-6-hydroxy-octanoic acid of formula (+)-(I), wherein X is Cl, (6.4 g, 32.9 mmoles) was refluxed for 2 hours in 100 ml of absolute methanol after the addition of 0.4 ml of concentrated hydrochloride. After that, the solvent was evaporated under vacuum. The methyl ester of (+)-8-chloro-6-hydroxy-octanoic acid of formula (+)-(II), wherein X is Cl, and R is methyl, was obtained in a yield of 6.6 g (97% of the theoretical yield). $[\alpha]_D^{20}$=+24.5° (c=1, ethanol), e.e. >99% ($^1$H-NMR).

EXAMPLE 8

(−)-8-Chloro-6-hydroxy-octanoic acid of formula (−)-(I), wherein X is Cl (7.7 g, 39.5 mmoles) was refluxed for 2 hours in 120 ml of absolute methanol after the addition of 0.5 ml of concentrated hydrochloric acid. After that, the solvent was evaporated under vacuum. The methyl ester of (−)-8-chloro-6-hydroxy-octanoic acid of formula (−)-(II), wherein X is Cl, and R is methyl, was obtained in a yield of 7.9 g (97% of the theoretical yield). $[\alpha]_D^{20}$=−24.5° (c=1, ethanol), e.e. >99% ($^1$H-NMR).

EXAMPLE 9

Racemic 8-chloro-6-hydroxy-octanoic acid of formulae (+)-(I), wherein X is Cl, (9.0 g, 46.3 mmoles) and 10.6 g (70.0 mmoles) of sodium iodide were dissolved in 100 ml of acetone and refluxed for 12 hours. The precipitate was filtered off and washed with 10 ml of acetone and the filtrate was concentrated to 30 ml. After that, 100 ml of diethyl ether were added, the solution washed with 10 ml of water and dried over sodium sulfate and the solvent evaporated under vacuum. The racemic 8-iodo-6-hydroxy-octanoic acid of formula (I), wherein X is I, was obtained in a yield of 12.1 g (91% of the theoretical yield).

EXAMPLE 10

(+)-8-Iodo-6-hydroxy-octanoic acid of formula (+)-(I), wherein X is I, (2.85 g, 10 mmoles) was dissolved at 60° C. in 30 ml of a 1:1 mixture of ethyl acetate and cyclohexane. Over a period of 5 minutes, 1.21 g (10 mmoles) of R-(+)-α-methylbenzylamine were added. The reaction mixture was cooled to 20° C. over a period of 1 hour. The precipitate was filtered off and washed twice with 3 ml of a 1:1 mixture of ethyl acetate and cyclohexane. The salt was dried under vacuum at 40° C.

The R-(+)-α-methylbenzylamine salt of (+)-8-iodo-6-hydroxy-octanoic acid of formula (+)/(+)-(III), wherein X is I was obtained in a yield of 4.01 g (99% of the theoretical yield); $[\alpha]_D^{20}$=+23.6° (c=1; ethanol), e.e. >99% (HPLC), solubility in the 1:1 mixture of ethyl acetate and cyclohexane: 0.07% (20° C.), melting point: 108°–111° C.

EXAMPLE 11

(−)-8-Iodo-6-hydroxy-octanoic acid of formula (−)-(I), wherein X is I, (2.85 g, 10 mmoles) was dissolved at 60° C. in 30 ml of a 1:1 mixture of ethyl acetate and cyclohexane. Over a period of 5 minutes, 1.21 g (10 mmoles) of R-(+)-α-methylbenzylamine were added. The reaction mixture was cooled to 20° C. over a period of 1 hour. The precipitate was filtered off and washed twice with 3 ml of a 1:1 mixture of ethyl acetate and cyclohexane. The salt was dried under vacuum at 40° C.

The R-(+)-α-methylbenzylamine salt of (−)-8-iodo-6-hydroxy-octanoic acid of formula (−)/(+)-(III), wherein X is I, was obtained in a yield of 3.93 g (97% of the theoretical yield); $[\alpha]_D^{20}$=−14.2° (c=1; ethanol), e.e. >99% (HPLC), solubility in the 1:1 mixture of ethyl acetate and cyclohexane: 0.50% (20° C.), melting point: 84°–86° C.

EXAMPLE 12

(−)-8-Iodo-6-hydroxy-octanoic acid of formula (−)-(I), wherein X is I, (2.85 g, 10 mmoles) was dissolved at 60° C. in 30 ml of a 1:1 mixture of ethyl acetate and cyclohexane. Over a period of 5 minutes, 1.21 g (10 mmoles) of S-(−)-α-methylbenzylamine were added and the reaction mixture was worked up as described in Example 10.

The S-(−)-α-methylbenzylamine salt of (−)-8-iodo-6-hydroxy-octanoic acid of formula (−)/(−)-(III), wherein X is I, was obtained in a yield of 4.02 g (99% of the theoretical yield); $[\alpha]_D^{20}$=−23.6° (c=1; ethanol), e.e. >99% (HPLC), solubility in the 1:1 mixture of ethyl acetate and cyclohexane: 0.07% (20° C.), melting point: 108°–111° C.

EXAMPLE 13

(+)-8-Iodo-6-hydroxy-octanoic acid of formula (+)-(I), wherein X is I, (2.85 g, 10 mmoles) was dissolved at 60° C. in 30 ml of a 1:1 mixture of ethyl acetate and cyclohexane. Over a period of 5 minutes, 1.21 g (10 mmoles) of S-(−)-α-methylbenzylamine were added and the reaction mixture was worked up as described in Example 10.

The S-(−)-α-methylbenzylamine salt of (+)-8-iodo-6-hydroxy-octanoic acid of formula (+)/(−)-(III), wherein X is I, was obtained in a yield of 3.90 g (96% of the theoretical yield); $[\alpha]_D^{20}$=+14.2° (c=1; ethanol), e.e. >99% (HPLC), solubility in the 1:1 mixture of ethyl acetate and cyclohexane: 0.50% (20° C.), melting point: 84°–86° C.

EXAMPLE 14

The R-(+)-α-methylbenzylamine salt of (+)-8-iodo-6-hydroxy-octanoic acid of formula (+)/(+)-(III), wherein X is I, (8.1 g) was suspended at 20° C. in 90 me of diethylether and then cooled in ice. With stirring, the pH was slowly adjusted to a value of 1 with 3N HCl, the salt going into solution. After a further 30 minutes, the phases were separated and the organic phase was washed once with 10 ml of 2N HCl and twice with 10 ml of water and dried over magnesium sulfate. After the solvent was removed under vacuum, 5.2 g (90% of the theoretical yield) of (+)-8-iodo-6-hydroxy-octanoic acid of formula (+)-(I), wherein X is I were obtained; $[\alpha]_D^{20}$=+24.7° (c=1; ethanol), e.e. >99%.

EXAMPLE 15

The S-(−)-α-methylbenzylamine salt of (−)-8-iodo-6-hydroxy-octanoic acid of formula (−)/(−)-(III), wherein X is I, (8.1 g) was suspended at 20° C. in 90 ml of diethylether and then cooled in ice. With stirring, the pH was slowly adjusted to 1 with 3N HCl, the salt going into solution. After a further 30 minutes, the phases were separated and the organic phase was washed once with 10 ml of 2N HCl and twice with 10 ml of water and dried over magnesium sulfate. After the solvent was removed under vacuum, 5.1 g (89% of the theoretical yield) of (−)-8-iodo-6-hydroxy-octanoic acid of formula (−)-(I), wherein X is I, were obtained; $[\alpha]_D^{20}$=−24.7° (c=1; ethanol) e.e. >99%.

We claim:

1. Enantiomerically substantially pure (+)- or (−)-8-halogen-6-hydroxy-octanoic acid enantiomer of the formula

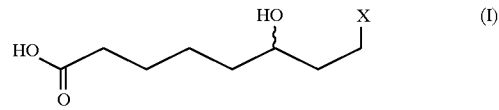

wherein X is Cl, Br, or I.

2. Alkyl ester of enantiomerically substantially pure (+)- or (−)-8-halogen-6-hydroxy-octanoic acid of the formula

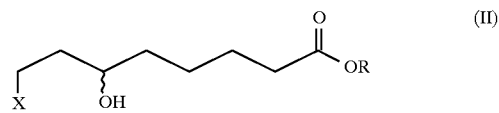

wherein X is as above, and R is a linear and branched $C_{2-6}$ alkyl residue.

3. Salts of the formula

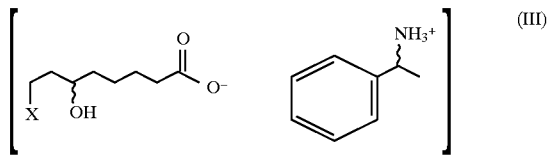

wherein X is Cl, Br, or I, from (+)- 8-halogen-6-hydroxy-octanoic acid, and R-(+)-α-methylbenzylamine, salts of formula (III), wherein X is Cl, Br or I, from (+)-8-halogen-6-hydroxy-octanoic acid, and S-(−) -α-methylbenzylamine, salts of formula (III), wherein X is Cl, Br or I, from (−)-8-halogen-6-hydroxy-octanoic acid and R-(+)-α-methylbenzylamine, salts of formula (III), wherein X is Cl, Br or I, from (−)-8-halogen-6-hydroxy-octanoic acid and S-(−)-α-methylbenzylamine.

* * * * *